United States Patent [19]

Binderman et al.

[11] Patent Number: 6,117,856

[45] Date of Patent: *Sep. 12, 2000

[54] TOPICAL BISPHOSPHONATES FOR PREVENTION OF BONE RESORPTION

[76] Inventors: Itzhak Binderman; Avinoam Yaffe, both of P.O. Box 2000, Rahway, N.J. 07065

[ * ] Notice: This patent issued on a continued prosecution application filed under 37 CFR 1.53(d), and is subject to the twenty year patent term provisions of 35 U.S.C. 154(a)(2).

[21] Appl. No.: 09/116,079

[22] Filed: Jul. 15, 1998

Related U.S. Application Data

[63] Continuation-in-part of application No. 08/800,004, Feb. 13, 1997, abandoned.
[60] Provisional application No. 60/011,632, Feb. 14, 1996.

[51] Int. Cl.⁷ ................................................... A61K 31/66
[52] U.S. Cl. .......................................... 514/108; 514/109
[58] Field of Search ..................................... 514/108, 109

[56] References Cited

U.S. PATENT DOCUMENTS

| | | | |
|---|---|---|---|
| 5,227,506 | 7/1993 | Saari et al. | 514/108 |
| 5,403,829 | 4/1995 | Lehtinen et al. | 514/102 |
| 5,668,120 | 9/1997 | Shinoda et al. | 514/102 |
| 5,681,590 | 10/1997 | Bechard et al. | 424/464 |
| 5,965,547 | 10/1999 | Goodship et al. | 514/102 |

FOREIGN PATENT DOCUMENTS

| | | |
|---|---|---|
| 0 198 213 A2 | 10/1986 | European Pat. Off. . |
| 0 388 220 A2 | 9/1990 | European Pat. Off. . |
| WO 93/11774 | 6/1993 | WIPO . |
| WO 95/28936 | 11/1995 | WIPO . |

OTHER PUBLICATIONS

Yaffe et al., J. Periodontal, vol. 66 (1995), p. 999–1003, "The effect of bisphosphonate on alveolar bone resorption following mucoperiosteal flap surgery in the mandible of rats".

Yaffe et al., Isr. Calcif. Tissue (Mar. 1995), Abstract, "Alendronate prevents alveolar bone resorption in rats".

Yaffe et al., J. Periodontol (1994), vol. 64, pp. 79–83, "Regional accelerated phenomenon in the mandible following mucoperiosteal flap surgery".

Physicians' Desk Reference (1995), Gelfoam, pp. 2548–2550.

*Primary Examiner*—Theodore J. Criares
*Attorney, Agent, or Firm*—Anthony D. Sabatelli; Joanne M. Giesser; Melvin Winokur

[57] ABSTRACT

Bisphosphonates inhibit bone resorption associated with periodonatal or orthopedic surgery when applied topically to the bone. A novel formulation for topical application contains a gelatin matrix which is soaked in a solution containing a bone absorption inhibiting effective amount of a bisphosphonate or a pharmaceutically acceptable salt.

5 Claims, No Drawings

TOPICAL BISPHOSPHONATES FOR PREVENTION OF BONE RESORPTION

CROSS REFERENCE TO RELATED APPLICATIONS

This is a continuation of U.S. Ser. No. 08/800,004, filed Feb. 13, 1997, which claims priority to U.S. Provisional Application Ser. No. 60/011,632 filed Feb. 14, 1996.

FIELD OF THE INVENTION

This invention relates to the topical application of bisphosphonates in the prevention of bone resorption following surgery or in the case of periodontal disease, and to topical formulations of bisphosphonates.

BACKGROUND OF THE INVENTION

To treat periodontitis, mucoperiosteal flaps are used to obtain access to bone and root surfaces. They are also used for debridement, pocket elimination, management of periodontal defects, implant surgery and in regenerative procedures. During the dissective procedure, the periosteum is usually separated from the alveolar bone proper, particularly in the area of the attached gingiva extending behind the mucogingival junction. A layer of lining cells remains attached to the bone surface, and the rest of the fibrous tissue layer is retained as part of the reflected flap. Many reports show that periodontal surgery stimulates osteoclastic activity with varying amounts of alveolar crest loss, unpredictably resulting in bone dehiscence and tooth loss.

In orthopedic surgery, as well as in periodontal surgery, striking bone remodeling activity occurs adjacent to the site of injury. This reaction has been termed "regional accelerated phenomenon" (RAP). It has been suggested that RAP occurs because osteoclasts (which resorb bone) and osteoblasts (which form new bone) do not exist in sufficient numbers to heal the bone following surgery.

Certain bisphosphonates have been used in the past to inhibit bone resorption. These include: clodronate, pamidronate, etidronate and alendronate. Alendronate is currently marketed in oral form as a treatment for postmenopausal osteoporosis, and others are marketed as systemic treatments of Paget's disease and conditions associated with bone cancers. Many bisphosphonates suffer from a low bioavailability, and in some cases the amount of bisphosphonate which must be delivered in order to produce a biological effect is so high that adverse side effects can occur.

Previously, the bisphosphonate alendronate (4-amino-1-hydroxy-butylidene 1,1,-bisphosphonic acid) was administered intravenously to prevent and treat periodontal disease (See U.S. Pat. No. 5,270,356).

U.S. Pat. No. 5,403,829 discusses the use of bisphosphonates, particularly clodronate, to enhance bone formation after oral or orthopedic surgery. Clodronate was delivered intramuscularly to the test animals.

Yaffe et al., 1995 J. Periodontology 66(11):999–1003 studied the effect of alendronate on alveolar bone resorption following surgery. Alendronate was administered either intravenously or using topical applications. While the intravenous administration was shown to reduce the amount of alveolar bone resorption, alendronate solutions applied topically were not found to be effective in inhibiting bone resorption.

It would be desirable to develop a topical bisphosphonate which can be directly applied to the site of bone injury which would prevent bone resorption, so that widespread systemic administration of bisphosphonates need not be used.

DESCRIPTION OF THE INVENTION

This invention is directed to a method of preventing or minimizing bone resorption following orthopedic or periodontal bone surgery comprising applying a topical bisphosphonate formulation to the bone, wherein the topical bisphosphonate formulation comprises a prophylactically or therapeutically effective amount of a bisphosphonate or a pharmaceutically acceptable salt thereof.

Yet another aspect of this invention is the use of a topical formulation for inhibiting bone resorption following periodontal or orthopedic surgery comprising a slow release matrix and a bisphosphonate or pharmaceutically accepted salt thereof.

Another aspect of this invention is a topical formulation for inhibiting bone resorption following periodontal or orthopedic surgery comprising a slow release matrix and a bisphosphonate or pharmaceutically acceptable salt thereof.

In a preferred aspect of this invention, the bisphosphonate compound is selected from the group consisting of alendronate, pamidronate, cimadronate, ibandronate, and etidronate, and their pharmaceutically effective salt forms, either alone or in combination. In a particularly preferred embodiment, the bisphosphonate is alendronate, and most preferred it is alendronate sodium.

Another aspect of this invention is a topical formulation of a bisphosphonate, suitable for application during surgery or periodontal disease treatment. The topical formulation will contain an active form of a bisphosphonate (either the anion, acid or salt) or mixture of bisphosphonates and a slow-release formulation material.

The slow release formulation material may be any material which is known to release the active ingredient over a relatively long period of time. It is also preferred that the slow-release formulation be soluble, and can adhere to bone. A preferred slow release material is a gelatin matrix which is commonly used in periodontal and orthopedic surgery and often referred to as an absorbable sterile sponge. One such material is marketed under the tradename GELFOAM® (Upjohn and Co.).

The bisphosphonate may be incorporated into the slow-release material in any know fashion. In a preferred embodiment of this invention, the bisphosphonate is dissolved in an aqueous solution, such as a saline solution, so that the aqueous solution contains a prophylactically or therapeutically effective amount of the bisphosphonate. The slow release matrix is soaked in the bisphosphonate solution for a period of time until it is substantially saturated, and then is applied to the bone.

It has been found, in accordance with this invention, that while a bisphosphonate dissolved in saline and applied topically for a short period of time is not effective in inhibiting bone resorption, a bisphosphonate which is in a slow release formulation is very effective in inhibiting bone formation, and surprisingly gives better results than a bisphosphonate administered systemically, even when the systemic administration is a larger dose.

Alendronate may be prepared according to any of the processes described in U.S. Pat. Nos. 5,019,651, 4,992,007, and WO 95/06052, published Mar. 2, 1995, each of which is hereby incorporated by reference. The pharmaceutically acceptable salts of alendronate include salts of alkali metals (e.g., Na, K), alkali earth metals (e.g. Ca), salts of inorganic acids, such as HCl and salts of organic acids such as citric acid and amino acids. Sodium salt forms are preferred, particularly the monosodium salt trihydrate form.

The slow release formulation will generally contain less bisphosphonate than is required for oral or i.v. formulations for treatment or prevention of bone resorption. The bisphosphonic acid solution will preferably comprise from about 0.01 to 2.0 mg/kg body weight of the bisphosphonate, and will vary with the relative activity of the bisphosphonate chosen. For example, with alendronate, the solution will comprise approximately 0.1 to 1.0 mg/kg body weight, and in a more preferred embodiment approximately 0.5 mg/kg body weight.

In addition to the slow release matrix and the bisphosphonate, the topical formulation may also include other suitable pharmaceutical diluents, excipients or carriers (collectively referred to herein as "carrier materials"). Moreover, when desired or necessary, suitable binders, disintegrating agents and the like can also be incorporated into the mixture of active ingredient(s) and inert carrier materials. Suitable binders may include starch, gelatin, natural sugars such as glucose, anhydrous lactose, free-flow lactose, beta-lactose, and corn sweeteners, natural and synthetic gums, such as acacia, tragacanth or sodium alginate, carboxymethyl cellulose, polyethylene glycol, waxes, and the like.

The following, non-limiting Examples are presented to better illustrate the invention.

EXAMPLE 1

25 Wistar rats were used in the following experiment. The right side of the mandible was used as the experimental side and the left side was used as the control.

The rats were anesthetized prior to surgery using a mixture of 25 mg/kg body weight of KETALAR (Malgene, Lyon, France) and 42 mg/kg body weight of XYLAZINE (Rampun Bayer, Leverkusen, Germany) intraperitoneally (IP).

A mucoperiosteal flap was made on both the buccal and lingual aspects in the region of premolars and molars on both sides of the mandible, two quadrants per rat. The flap was elevated using a special small periosteal elevator. A 1 mm diameter piece of GELFOAM (Upjohn Co., Kalamazoo, Mich.) which was soaked in 0.025 ml alendronate solution (below) was applied to the alveolar bone on both buccal and lingual aspects on the experimental (right) side and the flap was then readapted immediately in place without sutures.

The alendronate solution was prepared by dissolving 20 mg alendronate in 1 ml saline.

A GELFOAM pellet of 1 mm diameter, identical to the alendronate-soaked pellet, but lacking the alendronate, was applied to the alveolar bone in the control side. The entire procedure lasted about 20–40 seconds. The GELFOAM pellets remained in situ for at least two hours while the anesthesia was effected. The rats were fed a soft diet for 24 hours after surgery to avoid flap displacement. Rats were sacrificed 21 days after surgery.

High resolution X-ray microradiography analysis was performed. Ground sections were 1–1.5 mm thick, performed between premolar and molar region of the mandible in a buccal-lingual direction (4–5 sections in each side of the mandible). The X-ray analysis was performed in a mesio distal direction using KODAK Ektaspeed E safety film in a FAXITRON cabinet X-ray system (FAXITRON series Hewlett Packard) for 5 seconds and 20 KVP.

In the control side, a typical resorption of alveolar bone specifically on the crest and its periodontal ligament aspect resulted in excessive alveolar bone loss. If no other insult occurs, bone is restored to its original shape and volume after approximately three months.

On the experimental side, where alendronate was applied topically, bone resorption was inhibited.

COMPARATIVE EXAMPLE

63 Wistar rats were used in this experiment, and were divided into the four groups. Group A: 15 rats received 0.05 mg/kg body weight of alendronate. Group B: 15 rats received 0.25 mg/kg body weight of alendronate. Group C: 15 rats received 0.5 mg/kg body weight of alendronate. Group D was the control group, where 18 rats received saline. The alendronate sodium or saline was administered one week prior to surgery, at the day of surgery before the surgery was performed, and one week following surgery. The drug was administered IV in the dorsal vein of the penis.

In one experiment, one group of rats were anesthetized prior to surgery or alendronate administration using a mixture of 25 mg/kg body weight of KETALAR (Malgene, Lyon France), and 42 mg/kg body weight XYLAZINE (Rampun Bayer, Leverkusen, Germany) intraperitoneally (IP). A portion of these rats also received 25 mg/kg alendronate IP. The flap surgery was performed both on the buccal and lingual aspects of the region of premolars an molars on the right side of the mandible, one quadrant per rat. The flap was elevated using a special small periosteal elevator, and readapted immediately in place without sutures. Rats were fed a soft diet for 24 hours after surgery to avoid flap displacement.

In another set of experiments, alendronate was applied locally at three dose levels using a wet gauze sponge soaked with a solution of 0.15, 0.75, and 1.5 mg/ml on the exposed bone on the experimental side and saline on the exposed bone on the control side for 10 seconds. Since the sponge could absorb 0.1 ml, the maximum calculated amount of drug applied was 0.5 mg/kg body weight.

The rats were sacrificed 3 week following the flap procedure, and high resolution x-ray microradiographic analysis of 1 to 1.5 mm thick ground sections between premolar and molar region of the mandible in a buccal lingual direction were performed.

In rats which did not receive any alendronate, extensive bone resorption with loss of alveolar bone in more than 80% of the section was observed. In one group of rats, alendronate applied locally for 10 seconds directly on alveolar bone during surgery in three concentrations (0.15, 0.75, and 1.5 mg/ml) had no noticeable effect on reducing bone resorption. In rats which had received alendronate by IV (all doses) had reduced alveolar bone resorption.

What is claimed is:

1. A method of preventing or minimizing bone resorption following orthopedic or periodontal bone surgery comprising applying a topical bisphosphonate formulation directly to the bone, said topical bisphosphonate formulation comprising:

(a) a prophylactically or therapeutically effective amount of a bisphosphonic acid or a pharmaceutically acceptable salt thereof, and (b) a slow release matrix capable of adhering to bone.

2. A method according to claim 1, wherein the bisphosphonic acid or pharmaceutically acceptable salt thereof is selected from the group consisting of alendronate, pamidronate, cimadronate, ibandronate, and etidronate, their pharmaceutically acceptable salts, and mixtures thereof.

3. A method according to claim 2 wherein the alendronate or pharmaceutically acceptable salt thereof is alendronate or alendronate sodium.

4. A method according to claim 3, wherein the slow release matrix is a gelatin matrix.

5. A method according to claim 4 wherein the gelatin matrix is an absorbable gelatin sponge.

* * * * *